United States Patent [19]
Koelman et al.

[11] Patent Number: 5,923,171
[45] Date of Patent: Jul. 13, 1999

[54] DETERMINING A PARAMETER ON A COMPONENT IN A COMPOSITION

[75] Inventors: Johannes Maria Vianney Antonius Koelman; Andre De Kuijper, both of GD Rijswijk, Netherlands

[73] Assignee: Shell Oil Company, Houston, Tex.

[21] Appl. No.: 08/847,732

[22] Filed: Apr. 28, 1997

[51] Int. Cl.$^6$ .................................................. G01R 27/26
[52] U.S. Cl. ............................................ 324/439; 324/376
[58] Field of Search ................................. 324/439, 376, 324/323; 702/13; 73/152.06

[56] References Cited

U.S. PATENT DOCUMENTS

| | | | |
|---|---|---|---|
| 4,703,277 | 10/1987 | Kenyon | 324/338 |
| 4,903,207 | 2/1990 | Alger | 324/376 |
| 5,059,907 | 10/1991 | Sherman | 324/376 |
| 5,144,245 | 9/1992 | Wisler | 324/338 |

OTHER PUBLICATIONS

M. H. Waxman and L. J. Smits, "Electrical Conductivities in Oil Bearing Shaly Sands," SPE Paper 1863–A presented at 42$^{nd}$ Ann. Fall Meeting, Houston, Oct. 1–4, 1967.

P. N. Sen, C. Scala, and M. H. Cohen, "A self–similar model for sedimentary rocks with application to the dielectric constant of fused glass beds," *Geophysics*, vol. 46, No. 5 (May 1981), pp. 781–795, 9 FIGS.

M. H. Waxman and L. J. Smits, "Electrical Conductivities in Oil Bearing Shaly Sands," SPE Paper 1863–A presented at 42nd Ann. Fall Meeting, Houston, Oct. 1–4, Dec. 1967.

M. H. Waxman and L. J. Smits, "Electrical Conductivities in Oil Bearing Shaly Sands," SPE Paper 1863–A presented at 42nd Ann. Fall Meeting, Houston, Oct. 1–4, 1967.

*Primary Examiner*—Maura K. Regan

[57] ABSTRACT

A method of determining a parameter selected from the electrical conductivity and the volume fraction of a component in a composition comprising a plurality of components is provided. The method comprises measuring the electrical conductivity of the composition, and selecting a relationship between the conductivity of the composition and a plurality of composition parameters including, for each component, physical parameters representing the conductivity and the volume fraction of the component, said relationship being such that the components are substantially equally represented in said relationship by means of said physical parameters. The selected parameter of the component in the composition is determined by applying said relationship to the measured conductivity of the composition.

15 Claims, No Drawings

DETERMINING A PARAMETER ON A COMPONENT IN A COMPOSITION

FIELD OF THE INVENTION

The present invention relates to a method of determining a parameter selected from the electrical conductivity and the volume fraction of a component in a composition comprising a plurality of components. The invention is of particular interest for determining the volume fraction of a component of an earth formation, for example to determine the hydrocarbon-content of a hydrocarbon bearing earth formation. Various known methods of determining such content have been applied until now, which known methods are generally based on empirical models.

BACKGROUND TO THE INVENTION

One such known method is described in "Electrical conductivities in oil-bearing shaly sands", Waxman M. H. and Smits L. J. M., SPE paper 1863-A presented at 42nd Ann. Fall Meeting, Houston, October 1-4, 1967, hereinafter referred to as the SPE paper.

This publication discloses a method of determining a parameter selected from the electrical conductivity and the volume fraction of a component in a composition comprising a plurality of components, wherein the electrical conductivity of the composition is measured, and a relationship between the conductivity of the composition and the conductivity of a component is selected.

This known method uses the following relationship which is generally referred to as the Waxman-Smits model:

$$C_o = C_w/F^* + BQ_v/F^*$$

where $C_o$=conductivity of fully brine saturated rock $C_w$=conductivity of brine present in the formation $F^*$=a formation factor B=equivalent conductance of sodium clay-exchange cations as a function of $C_w$ $Q_v$=cation exchange capacity per unit pore volume.

The results achieved with this known method are not always sufficiently accurate, probably because of the empirical nature of the Waxman-Smits model which provides a relationship between the earth conductivity and the various other parameters.

It is an object of the invention to provide a more accurate method of determining a parameter selected from the electrical conductivity and the volume fraction of a component in a composition comprising a plurality of components.

SUMMARY OF THE INVENTION

The method according to the invention thereto comprises:

measuring the electrical conductivity of the composition;

selecting a relationship between the conductivity of the composition and a plurality of composition parameters including, for each component, physical parameters representing the conductivity and the volume fraction of the component, said relationship being such that the components are substantially equally represented in said relationship by means of said physical parameters; and determining said selected parameter of the component in the composition by applying said relationship to the measured conductivity of the composition.

It is to be understood that by the electrical conductivity is meant the electrical conductivity itself or any quantity derived therefrom, such as the electrical resistivity.

With the method according to the invention it is achieved that results of increased accuracy are provided. The selected relationship takes accurately account of the individual contributions of the components to the conductivity of the composition. The relationship applied in the method according to the invention is symmetrically in the components, i.e. no component is favored over another component. Moreover, it was found that the method according to the invention provides the desired accuracy for any percolation threshold of the components. In this respect it is to be understood that the amount of percolation of a component refers to the degree of continuity of the component in the composition. For example, vanishing percolation of a component implies that the component is fully dispersed in the composition, and full percolation of a component implies that the component is continuous throughout the composition.

DESCRIPTION OF A PREFERRED EMBODIMENT

Advantageously the plurality of composition parameters includes at least one fitting parameter, and wherein each fitting parameter is determined by applying said relationship to a data set obtained by measuring the electrical conductivity of at least one sample representative for said composition for various magnitudes of at least one of said parameters.

Preferably the plurality of parameters includes an auxiliary parameter depending on the geometrical configuration of the components in the composition.

Accurate geometrical representation by the auxiliary component is achieved if said auxiliary parameter is selected so as to be a function of a plurality of variables, each variable depending on the conductivity of one of said components and a mixing coefficient, whereby the mixing coefficients depend on the geometrical configuration of the components in the composition.

Advantageously the step of determining each fitting parameter by applying said relationship to the data set of the component is carried out through an iterative process. Suitably the iterative process includes repeatedly applying said relationship in a minimization scheme. The minimization scheme is preferably applied to an incoherence between the measured electrical conductivities of said components and the electrical conductivities of the components as determined through said relationship.

The invention will be described hereinafter in more detail and by way of the following example and comparative example.

EXAMPLE

Consider an isotropic system with essential spherical inclusions in the form of an earth formation which essentially consists of four components: non-conducting porous rock matrix, non-conducting hydrocarbon fluid, conducting clay, and conducting brine. The conductivity of the formation depends on the fractional brine saturation of the pore space, and the hydrocarbon fluid component is grouped with the rock matrix, both being non-conducting. Thus, the hydrocarbon component and the rock matrix component only enter the equations with the sum of their volume fractions. The effective conductivity $\sigma_{eff}$ of this earth formation is evaluated through the expression $$(\sigma_{eff} - \sigma_0) \cdot (L\sigma_{eff} + (1-L)\sigma_0)^{-1} = \Sigma \phi_k (\sigma_k - \sigma_0) \cdot (L\sigma_k + (1-L)\sigma_0)^{-1}$$

wherein $\sigma_0$ represents the auxiliary parameter in the form of a conductivity tensor k=1 . . . N, N being the number of components $\sigma_{eff}$ represents the conductivity tensor of the sample
$\sigma_k$ represents the conductivity tensor of component k
$\phi_k$ represents the volume fraction of component k
L represents the depolarization tensor Preferably the depolarization tensor is positive and has unit trace. In an attractive embodiment the depolarization tensor equals ⅓ times the unit tensor.

The term $\sigma_0$ denotes an auxiliary parameter which can be thought of as being an additional host medium into which components are added until the host medium has been completely replaced by the components so that no volume fraction is associated with the host medium. The existence of the host medium enables the model to be symmetrical in all its constituents: none of the components rock, clay or brine in the model is favored over any of the other components. The dependence of $\sigma_0$ on various parameters, yet to be determined, governs the percolation behavior of the model. Setting $\sigma_0 = \sigma_{brine}$ leads to the known Average T-matrix Approximation, also referred to as the generalized Clausius-Mossotti equation. This model has a clear asymmetry between the brine component and the other components since only the brine component will percolate, irrespective of its volume fraction. Selecting a self-consistent host medium conductivity, $\sigma_0 = \sigma_{eff}$, leads to the known Coherent Potential Approximation, also referred to as the generalized Bruggeman equation. This model is symmetrical in all components but has the drawback of requiring unrealistically high percolation thresholds for each component.

In a suitable embodiment, the auxiliary parameter as is selected as follows:

$$\sigma_0 = \Sigma h_k \sigma_k; \text{ for } k=1, 2, 3$$

wherein $h_k$ represents the mixing coefficient tensor pertaining to component k, which tensor contains mixing coefficients representing geometrical information on the spatial distribution of the components in the formation. These coefficients determine the connectivity, i.e. the amount of percolation of the individual components. The coefficients are non-negative and fulfill the normalization condition:

$$\Sigma h_k = 1; \text{ for } k=1, 2, 3$$

The normalization relation ensures that the resulting effective conductivity $\sigma_{eff}$ satisfies the Hashin-Shtrikman bounds, which are well known to those skilled in the art.

Furthermore, a component with a vanishingly small volume fraction can not percolate, hence the corresponding connectivity parameter should vanish:

$$\lim h_k = 0; \text{for } \phi_k \to 0$$

Suitably the mixing coefficient tensor is selected to be $$h_k = \lambda_k \phi_k^{v_k} (\Sigma \lambda_n \phi_n^{v_n})^{-1}$$

wherein k,n=1 ... N, N being the number of components in said plurality of components
$\lambda_k$ represents the percolation rate tensor pertaining to component k
$\phi_k$ represents the volume fraction of component k
$v$ represents the percolation exponent pertaining to component k Suitably at least one of $h_k$, $\lambda_k$ and $v$ forms a fitting parameter.

A data set on 27 shaly-sand core samples has been used to test the invention, which data set is described in the above indicated SPE paper. This publication provides $C_o$–$C_w$ curves on the core samples ranging from almost clean sand ($Q_v$=0.017 eq/l) to extremely shaly sand ($Q_{dv}$=1.47 eq/l). The samples contained Kaolinite, Montmorillonite and Illite, either in combination or separately in each sample. The characteristic petrophysical data of each sample are listed in the appended Table, in which $\phi$ denotes the porosity of the sample, $\kappa$ denotes the permeability of the sample, and $Q_v$ denotes the cation exchange capacity per unit pore volume of the sample. The conductivity of each sample in fully brine saturated condition was measured for eight to ten salinities of the brine. Furthermore, concentration membrane potential measurements were made of the samples.

The parameters in this model were selected as follows:
1) Brine;

The volume fraction of brine, $\phi_b$, is determined by the porosity, the amount of clay-bound water, and the water saturation $S_w$. The brine conductivity $\sigma_b$ (=$C_w$) is determined by the brine salinity and the brine temperature. The two percolation parameters, $\lambda_b$ and $v$, are free parameters.

2) Rock/Hydrocarbon;

The volume of hydrocarbons, $\phi_{hc}$ is determined by the total porosity, the amount of clay-bound water, and the hydrocarbon saturation 1-$S_w$, while the volume of the rock matrix, $\phi_r$, is calculated using the sum rule and the volume fractions. Both the rock and the hydrocarbon have vanishing conductivity. The percolation parameters $\lambda_r$ and $\lambda_{hc}$ of both components was set at value 1. The mixing coefficient pertaining to rock/hydrocarbon $h_{r/hc}$ follows from the condition $\Sigma h_k = 1$.

3) Clay;

The volume of clay $\phi_c$ and the clay conductivity $\phi_c$ are free fitting parameters. The percolation rate $\lambda_c$ was set at a value 0, which is a suitable choice for non-laminated clays. It furthermore appeared that an additional free parameter did not give a significant improvement of the model fit to the data set.

The $C_o$–$C_w$ measurements were made for an extreme salinity range, namely a brine salinity between 1–300 g/l. For a given sample the brine volume fraction varied only slightly over the whole salinity range. In view thereof the percolation parameter $v$ was set equal to unity in the test, thereby reducing the percolation parameter $h_b$ to a constant, and reducing the number of free parameters to three.

For each sample, a fit to the $C_o$–$C_w$ curve was made by minimizing the relative incoherence defined as:

$$\sum \Delta^2 C_o - C_w = \sum_{salinities} \left( \frac{C_{o,calc} - C_{o,meas}}{C_{o,meas}} \right)^2$$

wherein
$C_{o,calc}$=the calculated conductivity of the fully brine saturated rock samples;
$C_{o,meas}$=the measured conductivity of the fully brine saturated rock samples;
$\Sigma$=summation over the salinities.

The results for the three fitting parameters $\phi_c$, $\sigma_c$ and $h_b$, and the relative incoherence are given in the Table.

Furthermore, the Table gives the incoherence between the membrane potential ($\psi_{calc}$) determined by the method of the invention and the measured membrane potential ($\psi_{meas}$):

The membrane potential is a particularly interesting quantity for being a direct, non-destructive, measure of the clay contribution to the overall conductivity, which has not been $$\sum \delta^2{}_{MP} = \sum_{salinities} \left(\frac{\Psi_{calc} - \Psi_{meas}}{\Psi_{meas}}\right)^2$$

used to determine the fitting parameters.

To illustrate the invention more specifically, reference is made to the following comparative example.

Comparative Example

As stated above Ref. 1 discloses, apart from the data set on the 27 core samples, furthermore an empirical model which is generally referred to as the Waxman-Smits model. To compare the method according to the invention with the Waxman-Smits model, the relative incoherence between the measured conductivities and the conductivities found from the Waxman-Smits model, and the relative incoherence between the measured concentration membrane potentials and the concentration membrane potentials found from the Waxman-Smits model, were determined. These relative incoherences for all 27 samples are listed in the Table. In applying the Waxman-Smits model, use has been made of the well known expression:

$$C_o = C_w/F^* + BQ_v/F^* \text{ with } F^* = \phi^{-m}$$

where m is a free parameter (also referred to as the cementation exponent), $Q_v$ is determined from sample measurements, just as the porosity $\phi$, and the standard B-chart has been used to calculate the salinity and temperature effects on the conductivity measurements.

From a comparison between the incoherence values found by using the method according to the invention, and the incoherence values found by using the Waxman-Smits model, it is clear that the method according to the invention provides improved results. Especially the extremely low incoherence values for the concentration membrane potential, which values are moreover fairly constant over the entire $Q_v$ range, indicates that the method according to the invention provides results of increased accuracy.

The method according to the invention can suitably be applied to determine the volume fraction of brine or hydrocarbon in an earth formation, whereby a well-log representing the electrical conductivity of the formation is provided. Such application can, for example, be carried out in the following manner. The well-log of the electrical conductivity of the earth formation is made using a logging tool lowered in a borehole formed in the earth formation. For an isotropic formation with components brine (subscript B), clay (subscript C), and non-conducting rock+hydrocarbon (subscript R/HC) the rock and the hydrocarbon are grouped together because of their vanishing conductivities. The selected relationship then is:

$$\frac{\sigma_{eff} - \sigma_0}{\sigma_{eff} + 2\sigma_0} = \sum_{k=1}^{3} \phi_k \frac{\sigma_k - \sigma_0}{\sigma_k + 2\sigma_0}$$

wherein $$h_k = \lambda_k \phi_k^{v_k} (\Sigma \lambda_n \phi_n^{v_n})^{-1}$$

wherein $\sigma_0$ represents the auxiliary parameter k, n=1 ... N, N being the number of components $\sigma_{eff}$ represents the conductivity of the earth formation $\sigma_k$ represents the conductivity of component k $\phi_k$ represents the volume fraction of component k $h_k$ represents the mixing coefficient per g to component k;

$\lambda_k$ represents the percolation coefficient pertaining to component k;

$v_{k,n}$ represents the percolation exponent pertaining to component k,n;

Each component k has four parameters: $\phi_k$, $\sigma_k$, $\lambda_k$, and $v_k$, of which $\phi_B$, $\sigma_B$, and $\sigma_{R/HC}$ are directly measured. Furthermore, a priori is determined that $\lambda_c = 0$ for dispersed clay. From the sum rules $h_{R/HC}$ and $\phi_{R/HC}$ follow. Parameters which are yet to be determined are $\sigma_C$, $\lambda_B$, $v_B$ and $\phi_C$. These parameters are determined through forward modelling on experimental data. $\sigma_C$, $\lambda_B$ and $v_B$ are invariable over the geological formation, while $\phi_B$ will be depth dependent. The experimental data for the parameter determination consist of well-log measurements from a brine containing zone, laboratory Formation Resistivity Factor (FRF) measurements and brine saturation experiments. The log information from the brine containing zone is used to correlate the local parameter $\phi_C$ to suitable logs/log combinations, as is known to those skilled in the art of well logging. $\sigma_C$, $\lambda_B$ and $\phi_B$ and the correlation of $\phi_C$ to suitable logs/log combinations can be used in hydrocarbon bearing formations. From the well-log, the above relationship and the indicated parameters, the volume faction of brine and thus also the volume fraction of hydrocarbon is determined as a function of depth.

TABLE

| sample | petrophysical data | | | parameters | | | incoherence for present invention | | incoherence for prior art | |
|---|---|---|---|---|---|---|---|---|---|---|
| No. | $\phi$ | $\chi$ [mD] | $Q_v$ eq/l | $\phi_c$ | $\sigma_c$ [mS/cm] | $h_B$ | $\Sigma\Delta^2_{C_0-}$ | $\Sigma\Delta^2_\psi$ | $\Sigma\Delta^2_{C_0-C}$ | $\Sigma\Delta^2_\psi$ |
| 1 | 0.239 | 659 | 0.017 | 0.0532 | 2.9581 | 0.2016 | 0.002 | 0.018 | 0.009 | 0.026 |
| 2 | 0.212 | 105 | 0.052 | 0.1822 | 1.3537 | 0.2038 | 0.002 | 0.035 | 0.061 | 0.099 |
| 3 | 0.231 | 397 | 0.052 | 0.1376 | 1.8607 | 0.2517 | 0.002 | 0.014 | 0.031 | 0.097 |
| 4 | 0.080 | 1.34 | 0.26 | 0.1323 | 1.3325 | 0.1788 | 0.010 | 0.119 | 0.045 | 0.010 |
| 5 | 0.154 | 55 | 0.2 | 0.3216 | 1.4851 | 0.3752 | 0.005 | 0.042 | 0.149 | 0.128 |
| 6 | 0.215 | 29 | 0.095 | 0.3467 | 1.0193 | 0.1370 | 0.003 | 0.026 | 0.206 | 0.257 |
| 7 | 0.171 | 3.5 | 0.053 | 0.3779 | 0.7847 | 0.1200 | 0.008 | 0.016 | 0.312 | 0.446 |
| 8 | 0.171 | 7.66 | 0.053 | 0.3119 | 0.8994 | 0.1274 | 0.007 | 0.018 | 0.234 | 0.366 |
| 9 | 0.199 | 57 | 0.085 | 0.3935 | 1.0627 | 0.1613 | 0.007 | 0.025 | 0.276 | 0.351 |
| 10 | 0.125 | 0.042 | 0.253 | 0.432 | 0.3113 | 0.0255 | 0.029 | 0.074 | 0.483 | 0.262 |
| 11 | 0.125 | 0.0106 | 0.253 | 0.4007 | 0.2590 | 0.0233 | 0.037 | 0.057 | 0.348 | 0.203 |
| 12 | 0.110 | 1.86 | 0.28 | 0.5855 | 0.8601 | 0.1326 | 0.018 | 0.010 | 0.760 | 0.542 |
| 13 | 0.110 | 0.3 | 0.28 | 0.5998 | 1.0802 | 0.1286 | 0.020 | 0.016 | 0.868 | 0.589 |

TABLE-continued

| sample | petrophysical data | | | parameters | | | incoherence for present invention | | incoherence for prior art | |
|---|---|---|---|---|---|---|---|---|---|---|
| No. | φ | χ [mD] | $Q_v$ eq/l | $\phi_c$ | $\sigma_c$ [mS/cm] | $h_B$ | $\Sigma\Delta^2_{C_0-}$ | $\Sigma\Delta^2_\psi$ | $\Sigma\Delta^2_{C_0-C}$ | $\Sigma\Delta^2_\psi$ |
| 14 | 0.110 | 2.08 | 0.28 | 0.5815 | 1.4104 | 0.1998 | 0.054 | 0.029 | 0.854 | 0 s39 |
| 15 | 0.092 | 0.128 | 0.41 | 0.509 | 0.6025 | 0.0402 | 0.027 | 0.025 | 0.917 | 0 449 |
| 16 | 0.103 | 0.024 | 0.67 | 0.7202 | 1.4537 | 0.1103 | 0.010 | 0.013 | 1.263 | 0 529 |
| 17 | 0.140 | 0.575 | 0.33 | 0.7763 | 1.5783 | 0.0977 | 0.050 | 0.013 | 1.606 | 0 919 |
| 18 | 0.259 | 3.78 | 0.59 | 0.7033 | 2.8964 | 0.1357 | 0.012 | 0.007 | 1.173 | 0.507 |
| 19 | 0.259 | 17.1 | 0.59 | 0.6408 | 2.8227 | 0.1484 | 0.010 | 0.012 | 0.823 | 0.376 |
| 20 | 0.259 | 44.8 | 0.59 | 0.5978 | 3.4771 | 0.2113 | 0.003 | 0.023 | 0.674 | 0.286 |
| 21 | 0.238 | 315 | 0.29 | 0.6984 | 1.3859 | 0.1812 | 0.009 | 0.031 | 0.632 | 0.546 |
| 22 | 0.225 | 1.92 | 0.72 | 0.7651 | 2.4172 | 0.0766 | 0.016 | 0.013 | 1.808 | 0.637 |
| 23 | 0.242 | 54.3 | 1.04 | 0.7306 | 4.0758 | 0.1165 | 0.022 | 0.011 | 1.640 | 0.490 |
| 24 | 0.216 | 0.546 | 0.81 | 0.7751 | 2.6418 | 0.0659 | 0.021 | 0.014 | 2.103 | 0.703 |
| 25 | 0.187 | 0.0348 | 1.27 | 0.7995 | 3.4510 | 0.0726 | 0.005 | 0.040 | 0.490 | 0.369 |
| 26 | 0.229 | 1.53 | 1.47 | 0.7491 | 5.0425 | 0.0887 | 0.042 | 0.026 | 2.155 | 0.470 |
| 27 | 0.209 | 0.263 | 1.48 | 0.7656 | 5.1455 | 0.0884 | 0.001 | 0.067 | 0.495 | 0.326 |

We claim:

1. A method for determining a parameter selected from the electrical conductivity and the volume fraction of a component in a composition comprising a plurality of components, the method comprising the steps of:

measuring the electrical conductivity of the composition;

selecting a relationship between the conductivity of the composition and a plurality of composition parameters including, for each component, physical parameters representing the conductivity and the volume fraction of the component, said relationship being such that the components are substantially equally represented in said relationship by means of said physical parameters; and determining said selected parameter of the component in the composition by applying said relationship to the measured conductivity of the composition wherein said relationship is selected to be $$(\sigma_{eff}-\sigma_0).(L\sigma_{eff}+(1-L)\sigma_0)^{-1}=\Sigma\phi_k(\sigma_k-\sigma_0).(L\sigma_k+(1-L)\sigma_0)-1$$

wherein $\sigma_0$ represents the auxiliary parameter in the form of a conductivity tensor k=1 ... N, N being the number components $\sigma_{eff}$ represents the conductivity tensor of the sample $\sigma_k$ represents the conductivity tensor of component k $\phi_k$ represents the volume fraction of component k L represents a depolarization tensor, and $$\sigma_0 = \Sigma h_k \sigma_k$$

wherein $h_k = \lambda_k \phi_k^{vk}(\Sigma \lambda_n \phi_n^{vn})-1$ $\lambda_k$ represents a percolation rate tensor, a constant, pertaining to component k, and $v_k$ represents a percolation exponent, a constant, pertaining to component k.

2. The method of claim 1, wherein said plurality of composition parameters includes at least one fitting parameter, and wherein each fitting parameter is determined by applying said relationship to a data set obtained by measuring the electrical conductivity of at least one sample representative for said composition for various magnitudes of at least one of said parameters.

3. The method of claim 1 wherein at least one of $h_k$, $\lambda_k$ and v forms a fitting parameter.

4. The method of any of claim 1 wherein the depolarization tensor is positive.

5. The method of claim 1 wherein the depolarization tensor has unit trace.

6. The method of claim 1 wherein the depolarization tensor equals ⅓ times the unit tensor.

7. The method of claim 3 wherein the step of determining each fitting parameter by applying said relationship to the data set is carried out through an iterative process.

8. The method of claim 7 wherein the iterative process includes repeatedly applying said relationship in a minimization scheme.

9. The method of claim 8 wherein the minimization scheme is applied to a mismatch between the measured electrical conductivities of said components and the electrical conductivities of the components as determined through said relationship.

10. The method of claim 3 wherein said composition includes an earth formation.

11. The method of claim 10 wherein said earth formation includes at least one of rock, brine, hydrocarbon fluid and clay.

12. The method of claim 11 wherein said parameter which is determined forms the volume fraction of one of the hydrocarbon fluid and the brine.

13. A method for determining a volume fraction of oil in a formation, the method comprising the steps of:

a) obtaining a core representative of the formation;

b) determining clay volume fraction and porosity of the core;

c) measuring electrical conductivity of the core with the core containing brines at a plurality of different brine conductivities;

d) determining constants $\lambda_B$ and $v_B$ and the clay conductivity $\sigma_C$ from the core electrical conductivities at different brine conductivities by fitting the measured electrical conductivities as a function of brine conductivities to equations $$(\sigma_{eff}-\sigma_0).(L\sigma_{eff}+(1-L)\sigma_0)^{-1}=\Sigma\phi_k(\sigma_k-\sigma_0).(L\sigma_k+(1-L)\sigma_0)-1$$

wherein k=1 ... N, N being the number components $\sigma_{eff}$ represents the conductivity tensor of the sample $\sigma_k$ represents the conductivity tensor of component k $\phi_k$ represents the volume fraction of component k L represents a depolarization tensor, $$\sigma_0 = \Sigma h_k \sigma_k$$

wherein $h_k = \lambda_k \phi_k^{v_k} (\Sigma \lambda_n \phi_n^{v_n})^{-1}$ $\lambda_k$ represents a percolation rate tensor, a constant, pertaining to component k, and $v_k$ represents a percolation exponent, a constant, pertaining to component k;

e) determining, as a function of depth for at least a portion of the formation, the clay content of the formation;

f) determining, as a function of depth for at least a portion of the formation, the porosity of the formation;

g) determining the brine conductivity for the brine within the formation at formation conditions as a function of depth for at least a portion of the formation; and h) determining, using the relationships of step d), along with the porosity of step f) and the clay content of step e), and the brine conductivity from step g), the hydrocarbon content for at least a portion of the formation.

14. The method of claim 13 wherein the clay volume fraction of the core is determined by fitting the equations of step d) to the conductivity measurements at different brine conductivities with the clay volume fraction as a fitting parameter.

15. The method of claim 13 wherein the clay volume fraction of the core is determined by setting $\phi_{clay}$ as a fitting variable in step d).

* * * * *